United States Patent [19]

Rueter et al.

[11] 4,105,672

[45] Aug. 8, 1978

[54] PROCESS FOR THE PRODUCTION OF CYCLIC DIESTERS OF DODECANEDIOIC ACID

[75] Inventors: Joern Rueter; Klaus Burzin; Karl-Heinz Magosch; Roland Feinauer, all of Marl, Germany

[73] Assignee: Chemische Werke Huels Aktiengesellschaft, Marl, Germany

[21] Appl. No.: 734,013

[22] Filed: Oct. 19, 1976

[30] Foreign Application Priority Data

Oct. 22, 1975 [DE] Fed. Rep. of Germany ....... 2547267

[51] Int. Cl.² .................................... C07D 321/00
[52] U.S. Cl. ........................................ 260/340.2
[58] Field of Search ................................ 260/340.2

[56] References Cited

U.S. PATENT DOCUMENTS

| 2,092,031 | 9/1937 | Spanagel | 260/340.2 |
| 2,163,109 | 6/1939 | Spanagel | 260/340.2 |
| 3,431,279 | 3/1969 | Ehrhart | 260/340.2 |

FOREIGN PATENT DOCUMENTS

| 1,443,574 | 2/1969 | Fed. Rep. of Germany. | |
| 21,873 | 6/1971 | Japan | 260/340.2 |
| 69,088 | 6/1975 | Japan. | |
| 484,099 | 1/1970 | Switzerland | 260/340.2 |

OTHER PUBLICATIONS

Chemical Abstracts, vol. 72 (1970) 12133v.
Chemical Abstracts, vol. 77 (1972) 139625r.
Chemical Abstracts, vol. 83 (1975) 115656z.

*Primary Examiner*—Norma S. Milestone
*Attorney, Agent, or Firm*—Millen & White

[57] ABSTRACT

Cyclic esters of dodecanedioic acid with aliphatic diols of 2-12 carbon atoms in the chain and substituted by up to two alkyl of 1-4 carbon atoms, are produced by thermolysis of corresponding linear polyesters under reduced pressure in the presence of catalysts by subjecting the linear polyesters to thermolysis at temperatures between 200° and 300° C., and by utilizing as catalyst a tin(II) salt of an aliphatic monocarboxylic acid of up to 18 carbon atoms, of an aromatic or araliphatic monocarboxylic acid of up to 36 carbon atoms, of an aliphatic or aromatic hydroxy-, poly-, ketocarboxylic acid or of a dicarboxylic acid of up to 18 carbon atoms; or a mixture of an organotin compound of the formula

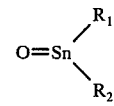

wherein $R_1$ and $R_2$ are alkyl of 1-18 carbon atoms, or aryl or aralkyl of 6-36 carbon atoms, and an O,O-dialkyl-(3,5-di-tert.-butyl-4-hydroxybenzyl)-phosphonate wherein each alkyl is of 2-18 carbon atoms.

14 Claims, No Drawings

PROCESS FOR THE PRODUCTION OF CYCLIC DIESTERS OF DODECANEDIOIC ACID

BACKGROUND OF THE INVENTION

The preparation of cyclic diesters by thermolysis of linear polyesters in the presence of catalysts is disclosed in French Pat. No. 796,410. The catalysts employed are inorganic salts, e.g., chlorides, nitrates, carbonates, and oxides of magnesium, manganese, iron, cobalt, and tin. Attempted preparation of cyclic diesters of dodecanedioic acid in this fashion gives yields of less than 25%.

Improved yields are obtained by the method of Japanese Laid-Open Application No. 4,826,790 and Japanese Published Application No. 4,920,503, wherein linear polyesters of dodecanedioic acid and ethylene glycol are treated with lead nitrate or lead dioxide, respectively, at 260°–280° C. under reduced pressure. Crude yields of up to 88% of cyclo(ethylenedodecanedioate) are obtained. However, lead compounds utilized as the catalysts are present in the reaction products in considerable amounts, even after a fine-distillation step.

Because the cyclic esters, owing to their odor characteristics, are utilized primarily in the cosmetic industry as fixatives, e.g., in perfumes, soaps, or mouthwashes, the presence of lead-containing contaminants in the esters used for these purposes is prohibited for physiological reasons. Furthermore, problems are encountered in removal and/or dumping of lead-containing residue from the thermolysis.

Therefore, there is a continuing need for a process for producing cyclic esters of dodecanedioic acid which are free of toxic, lead-containing residues.

SUMMARY OF THE INVENTION

This invention relates, in a process for the production of a cyclic ester of dodecanedioic acid and an aliphatic diol of 2–12 carbon atoms and substituted by up to two alkyl of 1–4 carbon atoms, by thermolysis of a corresponding linear polyester under reduced pressure in the presence of a catalyst, to the improvement which comprises conducting the thermolysis at a temperature of from 200° to 300° C., and employing as the catalyst, (a) a tin(II) salt of an aliphatic monocarboxylic acid of up to 18 carbon atoms, an aromatic or araliphatic monocarboxylic acid of up to 36 carbon atoms, of an aliphatic or aromatic hydroxy-, poly-, ketocarboxylic or dicarboxylic acid of up to 18 carbon atoms; or (b) a mixture of an organotin compound of the formula

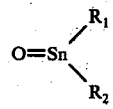

wherein $R_1$ and $R_2$ each are alkyl of 1–18 carbon atoms, or aryl or aralkyl of 6–36 carbon atoms, and an O,O-dialkyl-(3,5-di-tert.-butyl-4-hydroxybenzyl)-phosphonate wherein each alkyl is of 2–18 carbon atoms.

DETAILED DESCRIPTION

Linear polyesters of dodecanedioic acid used as starting compounds can be prepared by methods well known to any person skilled in the art, as disclosed, for example, by Korshak and Vinogradova in "Polyesters," Pergamon Press (1965), pp. 153 et seq. Some of these linear polyesters are commercially available.

The diol component of the polyester is any aliphatic diol of 2–12, preferably 2–6 carbon atoms, in the chain. The diol can additionally be substituted by up to 2 alkyl, each of up to 4 carbon atoms.

The diol component is a substituted ethylene, propylene, butylene, pentylene, hexylene, heptylene, octylene, nonylene, decylene, undecylene or dodecylene glycol, wherein the alcohol functions are primary or secondary, e.g., 1,2-or 1,3-propanediol, 1,4- or 1,3-butanediol, 1,8-octanediol, 1,10-decanediol and 1,12-dodecanediol.

Especially preferred diols are ethylene glycol, 1,2-propanediol, 1,3-propanediol, 1,4-butanediol, 1,6-hexanediol, 2,2-dimethyl-1,3-propanediol, 3,3-dimethyl-1,5-pentanediol, 2,2-diethyl-1,3-propanediol, and 2-n-butyl-2-ethyl-1,3-propanediol.

To avoid formation of excessive by-products of the thermolysis, the linear polyester should be very pure, that is, the diol and the dodecanedioic acid should be of fiber grade quality, e.g., the amount of dicarboxylic acid in the dodecanedioic acid is at least 99.9%.

It is advantageous to utilize polyesters having an acid number lower than about 10 mg. KOH/g. in order to prevent, to the extent possible, secondary reactions due to the presence of carboxyl end groups. The average degree of polymerization is between 3 and 200, preferably between 10 and 50, since polyesters of this degree of polymerization are readily manipulatable owing to their melt viscosity range.

The temperature required for the thermolysis ranges between 200° and 300° C. Below 200° C., the thermolysis velocity is too low, and above 300° C., undesired cracking reactions occur. A particularly preferred range is between 250° and 280° C. In this range, a rapid splitting of cyclic diesters occurs without undesired cracking reactions.

In order to remove the reaction product at a maximum rate from the reaction zone, thus preventing the product from undergoing secondary reactions, the thermolysis is effected under subatmospheric pressure. Preferably, a pressure is selected equal to or below the vapor pressure of the reaction product at the reaction temperature, so that the thus-formed product is immediately distilled from the reaction mixture. The pressure at which a quick distillation occurs depends somewhat on the reaction temperature. Good results are found at a temperature of 230° C = 0.1 mbar, of 250° C = 0.5 mbar, of 270° C = 0.8 mbar and 290° C = 3.0 mbar). The reaction most preferably is done at a pressure below 1 millibar.

One set of catalysts for the reaction are salts of bivalent tin with aliphatic monocarboxylic acids of up to 18 carbon atoms or aromatic or araliphatic monocarboxylic acids of up to 36 carbon atoms, and tin(II) salts of aliphatic or aromatic hydroxy-, poly-, ketocarboxylic or dicarboxylic acids of up to 18 carbon atoms.

Examples of salts of bivalent tin are salts with acetic, propionic, butyric, isobutyric, valeric, isovaleric, octanoic, decanoic, undecanoic, lauric, palmitic, stearic, benzoic, α-naphthoic, β-naphthoic, hydroxyethanoic, 2-hydroxypropanoic, 3-hydroxybutanoic, pyruvic, acetoacetic, levulinic, tartaric, citric, oxalic, malonic, adipic, dodecanedioic, phthalic, isophthalic, terephthalic, naphthalic, and naphthalenedicarboxylic acids.

Of these tin(II) salts, tin(II) acetate, tin(II) octoate, tin(II) laurate, tin(II) stearate, tin(II) palmitate, tin(II) adipate, tin(II) dodecanedioate, and tin(II) lactate, are preferred.

Another set of suitable catalysts are organotin compounds of the formula

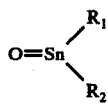

in admixture with an O,O-dialkyl-(3,5-di-tert.-butyl-4-hydroxybenzyl)phosphonate. In the formula

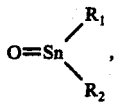

$R_1$ and $R_2$ each are alkyl of 1-18 carbon atoms, e.g., methyl, ethyl, propyl, butyl, isobutyl, pentyl, hexyl, octyl, nonyl, dodecyl, pentadecyl, and octadecyl. $R_1$ and $R_2$ can also be aryl or aralkyl 6-36 carbon atoms, for example, phenyl, benzyl, naphthyl, or toluyl. The organotin compound compound and the O,O-dialkyl-(3,5-di-tert.-butyl-4-hydroxybenzyl)phosphonate each are used in an amount of, e.g., 0.1-5% by weight, preferably 1-3% by weight of the polyesters.

Preferred organotin compounds are dibutyltin oxide, dioctyltin oxide, didodecyltin oxide, dipentadecyltin oxide, dioctadecyltin oxide, diphenyltin oxide, and dibenzyltin oxide.

Catalysts are generally mixed with the polyester before the thermolysis which is carried out in a conventional vacuum distillation apparatus. Since cyclic esters produced by the reaction are released into the vapor phase from the molten reaction mixture at the pressures employed, the process can be facilitated and the reaction time reduced by agitating the reaction mixture.

During thermolysis using organotin compounds as cataysts, the reaction mixture soon becomes so viscous that agitation is no longer possible. It has been found that this reaction mixture remains in a thinly fluid state for a considerably longer period of time if an O,O-dialkyl-(3,5-di-tert.-butyl-4-hydroxybenzyl)-phosphonate, alkyl of which are of 2-18 carbon atoms, is added to catalysts of the type

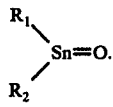

These compounds are readily available and are sold commercially. The can be prepared by esterification of 3,5-di-tert.-butyl-4-hydroxybenzylphosphonic acid with aliphatic alcohols in the presence of usual esterification catalysts. The amount of phosphonate added ranges between 0.1 and 5% by weight, based on the polyester. Below 0.1% by weight, their effect is too weak, and above 5% by weight, the effect no longer increases appreciably. Good results are achieved with added quantities between 1 and 3% by weight.

Because the reaction mixture remains fluid for a longer period of time, the agitation period can be extended. In case of large batches, this is of considerable advantage. Shortening of the reaction time is also attained, for example, from 5-7 hours to 4-5 hours. A further advantage of adding an O,O-dialkyl-(3,5-di-tert.-butyl-4-hydroxybenzyl)-phosphonate is that continuous thermolysis in a thin-film evaporator or in a vacuum extruder is facilitated, owing to improved fluidity characteristics of the reaction mixture.

In one preferred embodiment, the process as outlined above is that wherein the catalyst is tin(II) acetate, octoate, laurate, stearate, palmitate, adipate, dodecanedioate, or lactate, in an amount of 1-3% by weight of the polyester; the aliphatic diol is ethylene glycol, 1,2-propanediol, 1,3-propanediol, 1,4-butanediol, 1,6-hexanediol, 2,2-dimethyl-1,3-propanediol, 3,3-dimethyl-1,5-pentanediol, 2,2-diethyl-1,3-propanediol or 2-n-butyl-2-ethyl-1,3-propanediol; the polyester has a degree of polymerization of 10-50; the temperature is from 250° to 280° C.; said thermolysis is done at a pressure below 1 millibar; and a mixture of said polyester and said catalyst is agitated during said thermolysis.

In another preferred embodiment, the process as outlined above is that wherein the catalyst is dibutyl-, dioctyl-, dilauryl-, dipentadecyl-, distearyl-, diphenyl-, or dibenzyltin oxide in a mixture with O,O-dioctadecyl-(3,5-di-tert.-butyl-4-hydroxybenzyl)phosphonate, each in an amount of 1-3% by weight of the polyester; the aliphatic diol is ethylene glycol, 1,2-propanediol, 1,3-propanediol, 1,4-butanediol, 1,6-hexanediol, 2,2-dimethyl-1,3-propanediol, 3,3-dimethyl-1,5-pentanediol, 2,2-diethyl-1,3-propanediol or 2-n-butyl-2-ethyl-1,3-propanediol; the polyester has a degree of polymerization of 10-50; the temperature is from 250° to 280° C.; said thermolysis is done at a pressure below 1 millibar; and a mixture of said polyester and said catalyst is agitated during said thermolysis.

The major advantage of the present process is that, for the first time, cyclic esters of dodecanedioic acid free of toxic, hard-to-remove lead compounds can be prepared in high yields.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

In a distillation flask of a conventional vacuum distillation apparatus, 100 g. of a polyester of dodecanedioic acid and ethylene glycol, having a degree of polymerization of 31 and an acid number of 7 mg. KOH/g., was mixed intimately with 3.0 g. of $(CH_3COO)_2Sn$. The mixture is heated under a vacuum of below 1 millibar to 270° C. Cyclic diester is distilled over while the polyester foams. The thermolysis is terminated after 5-7 hours. The crude yield of 1,4-dioxacyclohexadecane-5,16-dione is 80%, based on polyester. For purification, the produce is taken up in 200 ml. of ether and washed twice with 50 ml. of $H_2O$. After drying the ether solution over $MgSO_4$, the ether is removed and residue is distilled. Yield of pure product: 73%.

B.p.$_{0.05}$ 117° C. $n_D^{20}$ 1.4721

EXAMPLES 2-4

Example 1 was repeated, varying the quantity and type of catalysts. Results are compiled in the table.

TABLE 1

| Example | Catalyst | Crude Yield |
|---------|----------|-------------|
| 2 | 2 g. Sn (C$_7$H$_{15}$COO)$_2$ | 78% |
| 3 | 3 g. Sn (C$_{17}$H$_{35}$COO)$_2$ | 81% |
| 4 | 3 g. Sn [CH$_3$CH(OH)COO]$_2$ | 75% |

EXAMPLE 5

In a conventional 500 ml stirred apparatus whose reflux condenser has been replaced by a distillation bridge, 100 g. of a polyester of dodecanedioic acid and 1,3-propanediol having a degree of polymerization of 21 and an acid number of 8 mg. KOH/g, was mixed vigorously with 3.0 g of dibutyltin oxide and 3 g. of O,O-dioctadecyl-(3,5-di-tert.-butyl-4-hydroxybenzyl)phosphonate. The resulting mixture was subjected to thermolysis at a pressure of 0.3 mbar and a temperature of 270° C. When the reaction mixture could not be stirred any longer (after about 4 hours), the reaction was terminated.

The crude yield of 1,5-dioxacycloheptadecane-6,17-dione is 65%, based on polyester.

B.p.$_{0.8}$ 155° C. n$_D^{20}$ 1.4690

Using dibutyltin oxide alone, the reaction takes 5 hours, i.e., the reaction time is 25% longer.

EXAMPLE 6

In accordance with Example 5, a polyester of dodecanedioic acid and 2,2-dimethyl-1,3-propanediol, degree of polymerization 25, acid number 7 mg. KOH/g., was subjected to thermolysis at 270° C. under an absolute pressure of 0.2 mbar for 4 hours. The crude yield of 1,5-dioxa-3,3-dimethylcycloheptadecane-6,17-dione is 50%, based on polyester. After recrystallization from methanol, the melting point of the pure cyclic ester is 50° C.

Analogous results are obtained with mixtures of 3 g. of dibutyltin oxide with 1 g. of O.O-didecyl-(3.5-di-tert.-butyl-4-hydroxybenzyl) phosphonate; 3 g. of dilauryltin oxide with 3 g. of O.O-dioctadecyl-(3.5-di-tert.-butyl-4-hydroxybenzyl) phosphonate; 3 g. of diphenyltinoxide with 3 g. of O,O-dioctyl-(3,5-di-tert.-butyl-4-hydroxybenzyl) phosphonate; or 3 g. of dioctadecyltin oxide with 3 g. of O,O-didodecyl-(3,5-di-tert.-butyl-4-hydroxybenzyl)phosphonate.

EXAMPLE 7

In a conventional 500 ml. agitator-equipped apparatus, the reflux condenser of which was replaced by a distillation heat, 100 g. of a polyester of dodecanedioic acid and ethylene glycol having an average degree of polymerization of 31 and acid number 7 mg. KOH/g., was mixed with 3 g. of dibutyltin oxide and 3 g. of O,O-dioctadecyl-(3,5-di-tert.-butyl-4-hydroxybenzyl)-phosphonate. The mixture is heated under a vacuum of 0.5 mbar and under agitation to 270° C., during which cyclic diester distils over while the polyester foams. The thermolysis is continued until the reaction mixture clings to the agitator and thus can no longer be stirred. This occurs after about 4–5 hours of reaction at 270° C. The yield of crude 1,4-dioxacyclohexadecane-5,16-dione is, at this time, 70%, based on the polyester. By further heating without stirring, the yield can be raised to about 83%.

B.p.$_{0.05}$ 117° C. n$_D^{20}$ 1.4721

In the same way, 1,6-dioxacyclooctadecane-7,18-dione (b.p.$_{0.3}$ 152° C.; n$_D^{20}$ 1.4699) and 1,8-dioxacycloeicosane-9,20-dione (b.p.$_{0.2}$ 167° C.; n$_D^{20}$ 1.4711) were produced.

COMPARATIVE EXAMPLES 1–10

In the distillation flask of a conventional vacuum distillation apparatus, 100 g. of a polyester of dodecanedioic acid and ethylene glycol having an average degree of polymerization of 31 and acid number 7 mg. KOH/g., was mixed with 3 g. of catalyst disclosed in French Pat. No. 796,410, indicated in Table 1, and subjected to thermolysis at 270° C. for 7 hours under a vacuum lower than 1 mbar. The following crude yields of 1,4-dioxacyclohexadecane-5,16-dione were obtained, based on polyester (Table 2):

TABLE 2

| Comp. Example | Catalyst | Crude Yield (%) |
|---------------|----------|-----------------|
| 1 | SnCl$_2$ . 2 H$_2$O | 13 |
| 2 | MnCl$_2$ . 4 H$_2$O | 16 |
| 3 | FeCl$_2$ . 4 H$_2$O | 23 |
| 4 | MgCl$_2$ . 6 H$_2$O | 12 |
| 5 | CoCl$_2$ . 6 H$_2$O | 19 |
| 6 | Co(NO$_3$)$_2$ . 6 H$_2$O | 14 |
| 7 | MnCO$_3$ | 25 |
| 8 | MgO | 13 |
| 9 | MgCO$_3$ | 9 |
| 10 | Mg Powder | 7 |

COMPARATIVE EXAMPLE 11

In the distillation flask of a customary vacuum distillation apparatus, 100 g. of a polyester of dodecanedioic acid and ethylene glycol having a degree of polymerization of 31 and acid number 7 mg. KOH/g., is mixed with 3 g. of PbO$_2$ and subjected to thermolysis under a vacuum below 1 mbar at 270° C. for 7 hours. The crude yield of 1,4-dioxacyclohexadecane-5,16-dione is 74%, based on polyester. The crude product contains 300 mg./kg. of lead. After a distillation, the lead content of the cyclic ester is still 100 mg./kg.

COMPARATIVE EXAMPLE 12

Comparative Example 11 is repeated using Pb(NO$_3$)$_2$ as catalyst. The crude yield of 1,4-dioxacyclohexadecane-5,16-dione is 79%, based on polyester. The lead content of the crude product is 500 mg./kg. After distillation, lead content is 150 mg./kg.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of a cyclic ester of dodecanedioic acid and an aliphatic diol of 2–12 carbon atoms and substituted by up to two alkyl of 1–4 carbon atoms, by thermolysis of a corresponding linear polyester under reduced pressure in the presence of a catalyst, the improvement which comprises conducting the thermolysis at a temperature of from 200° to 300° C., and employing as the catalyst a mixture of an organotin compound of the formula

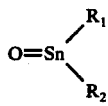

wherein $R_1$ and $R_2$ are each alkyl of 1–18 carbon atoms, or aryl or aralkyl of 6–36 carbon atoms, and an O,O-dialkyl-(3,5-di-tert.-butyl-4-hydroxybenzyl)phosphonate wherein each alkyl is of 2–18 carbon atoms.

2. The process of claim 1, wherein each of the organotin compound and O,O-dialkyl-(3,5-di-tert.-butyl-4-hydroxybenzyl)phosphonate are used in an amount of 0.1–5% by weight of the polyester.

3. The process of claim 1, wherein each of the organotin compound and O,O-dialkyl-(3,5-di-tert.-butyl-4-hydroxybenzyl)phosphonate are used in an amount of 1–3% by weight of the polyester.

4. The process of claim 1, wherein the catalyst is dibutyl-, dioctyl-, dilauryl-, dipentadecyl-, distearyl-, diphenyl- or dibenzyltin oxide in a mixture with O,O-dioctadecyl-(3,5-di-tert.-butyl-4-hydroxybenzyl)phosphonate.

5. The process of claim 1, wherein the catalyst is dibutyl-, dioctyl-, dilauryl-, dipentadecyl-, distearyl-, diphenyl- or dibenzyltin oxide in a mixture with O,O-dioctadecyl-(3,5-di-tert.-butyl-4-hydroxybenzyl)phosphonate, each in an amount of 1–3% by weight of the polyester.

6. The process of claim 1, wherein the aliphatic diol is of 2–6 carbon atoms in the chain.

7. The process of claim 1, wherein the aliphatic diol is ethylene glycol, 1,2-propanediol, 1,3-propanediol, 1,4-butanediol, 1,6-hexanediol, 2,2-dimethyl-1,3-propanediol, 3,3-dimethyl-1,5-pentanediol, 2,2-diethyl-1,3-propanediol or 2-n-butyl-2-ethyl-1,3-propanediol.

8. The process of claim 1, wherein the polyester has a degree of polymerization of 3–200.

9. The process of claim 1, wherein the polyester has a degree of polymerization of 10–50.

10. The process of claim 1, wherein the temperature is from 250° to 280° C.

11. The process of claim 1, wherein said thermolysis is done at a pressure below 1 millibar.

12. The process of claim 1, wherein a mixture of the polyester and the catalyst is agitated during the thermolysis.

13. The process of claim 1, wherein the catalyst is a mixture of the organotin compound and the O,O-dialkyl-(3,5-di-tert.-butyl-4-hydroxybenzyl)phosphonate and said thermolysis is carried out continuously in a thin-film evaporator or vacuum extruder.

14. The process of claim 1, wherein the catalyst is dibutyl-, dioctyl-, dilauryl-, dipentadecyl-, distearyl-, diphenyl- or dibenzyltin oxide in a mixture with O,O-dioctadecyl-(3,5-di-tert.-butyl-4-hydroxybenzyl)phosphonate, each in an amount of 1–3% by weight of the polyester; the aliphatic diol is ethylene glycol, 1,2-propanediol, 1,3-propanediol, 1,4-butanediol, 1,6-hexanediol, 2,2-dimethyl-1,3-propanediol, 3,3-dimethyl-1,5-pentanediol, 2,2-diethyl-1,3-propanediol or 2-n-butyl-2-ethyl-1,3-propanediol; the polyester has a degree of polymerization of 10–50; the temperature is from 250° to 280° C; said thermolysis is done at a pressure below 1 millibar; and a mixture of said polyester and said catlayst is agitated during said thermolysis.

* * * * *